United States Patent [19]

Diehr et al.

[11] 4,082,822
[45] Apr. 4, 1978

[54] PREPARATION OF DITHIOPHOSPHORIC ACID ESTER DIHALIDES

[75] Inventors: Hans-Joachim Diehr; Hermann Arold, both of Wuppertal, Germany

[73] Assignee: Bayer Aktiengesellschaft, Leverkusen, Germany

[21] Appl. No.: 704,254

[22] Filed: Jul. 12, 1976

[30] Foreign Application Priority Data

Jul. 19, 1975 Germany .............................. 2532396

[51] Int. Cl.² ........................... C07F 9/20; C07F 9/58; C07F 9/65
[52] U.S. Cl. ................................................... 260/972
[58] Field of Search .................... 260/972, 960, 251 P, 260/294.8 K, 304 R

[56] References Cited

U.S. PATENT DOCUMENTS 3,879,500  4/1975  Uhing et al. ..................... 260/960 X

FOREIGN PATENT DOCUMENTS 187,785  12/1966  U.S.S.R. ............................... 260/960

*Primary Examiner*—Richard L. Raymond
*Attorney, Agent, or Firm*—Burgess, Dinklage & Sprung

[57] ABSTRACT

A process for the preparation of a dithiophosphoric acid ester dihalide of the formula $$R-S-\overset{\overset{\displaystyle S}{\|}}{P}X_2$$

in which
X is chlorine, bromine, fluorine or iodine, and
R is an alkyl radical with up to 15 carbon atoms optionally substituted by halogen, by alkoxy or by alkylthio, a cycloaliphatic radical with 5 or 6 ring members, an aralkyl radical with 7 to 15 carbon atoms or an aryl or heterocyclic radical, comprising reacting a thiol compound of the formula $$R-SH$$

with a thiophosphoryl halide of the formula $$PSX_3$$

in the presence of a catalyst selected from the group consisting of a metal, an anhydrous metal halide, a Lewis acid, a nitrogen-alkylated lactam or an N,N-disubstituted carboxylic acid amide or phosphoric acid amide at a temperature of about 0° to 170° C.

10 Claims, No Drawings

PREPARATION OF DITHIOPHOSPHORIC ACID ESTER DIHALIDES

The present invention relates to an unobvious process for the preparation of dithiophosphoric acid ester dihalides, which can be used as intermediates for the synthesis of insecticidal active compounds.

It is already known that dithiophosphoric acid alkyl ester dichlorides can be prepared in moderate yields by heating the corresponding phosphoric acid alkyl ester dichlorides with phosphorus(V) sulfide to 140°–150° C (see Houben-Weyl: "Die Methoden der Organischen Chemie" ("The Methods of Organic Chemistry"), Volume 12/2, page 682 [1964], Georg Thieme Verlag Stuttgart).

As an intermediate stage in this process, the phosphoric acid alkyl ester dichlorides and phosphorus(V) sulphide form thiophosphoric acid O-alkyl ester dichlorides, which, according to the equation shown below, can also be reacted directly with phosphorus(V) sulphide, in a variant of the process, to give the dithiophosphoric acid alkyl ester dichlorides.

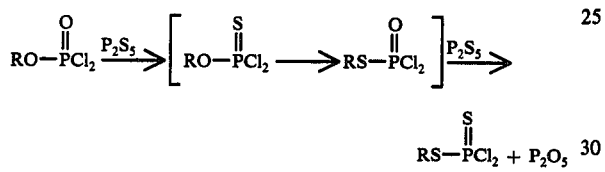

In carrying out these processes industrially, difficulties arise owing to the need to separate off, and remove, the phosphorus pentoxide which is formed alongside the dithiophosphoric acid alkyl ester dichlorides. The phosphorus pentoxide which remains as a solid after separating off the dithiophosphoric acid alkyl ester dichlorides still contains sulphur-containing, extremely malodorous compounds. Their removal to leave an odor-free product, say by oxidation in an alkaline medium, is only partially feasible, and requires long times and high costs.

Dithiophosphoric acid aryl ester dichlorides are not obtainable in accordance with the processes described above since the corresponding thiophosphoric acid O-aryl ester dichlorides do not rearrange on heating to give the thiophosphoric acid S-aryl ester dichlorides.

A further known method of synthesis for the preparation of dithiophosphoric acid ester dichlorides is the reaction of the thiophosphorous acid ester dichlorides, obtainable from thiols and phosphorus trichloride, with elementary sulphur.

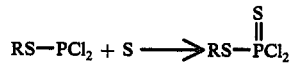

Since the addition reaction of sulphur with the thiophosphorous acid ester dichlorides only takes place at temperatures above 100° C, the sulphurization of the thiophosphorous ester dichlorides is associated with a marked isomerization to dithiophorous acid diester chlorides and phosphorus trichloride. In order to repress this side reaction, the sulphurization must be carried out under pressure (see Houben-Weyl, loc. cit.).

A possible means of preparing dithiophosphoric acid ester dichlorides by a simple method, by reaction of the corresponding thiol compounds with thiophosphoryl chloride, is described in U.S. Pat. No. 3,879,500 and Russian Pat. No. 187,785. If too large an amount of thiol compound is employed in this reaction, trithiophosphoric acid diester chlorides and tetrathiophosphoric acid esters are obtained almost exclusively as the reaction product, even in the presence of acid-binding agents (see also Houben-Weyl, loc. cit.).

The present invention now provides a highly efficient process for the preparation of a dithiophosphoric acid ester dihalide of the general formula

in which
X represents chlorine, bromine, fluorine or iodine, and
R represents a straight-chain or branched alkyl radical with up to 15 carbon atoms (which is optionally substituted by halogen, alkoxy or alkylthio), a cycloaliphatic radical with 5 or 6 ring members, an aralkyl radical with 7 to 15 carbon atoms or an aryl or heterocyclic radical which can be substituted by one or more functional groups, preferably halogen, $C_1$–$C_4$-alkoxy, $C_1$–$C_4$-alkyl, methylmercapto, trifluoromethyl or nitro, in which a thiol compound of the general formula

in which
R has the above-mentioned meaning,
is reacted with a thiophosphoryl halide of the general formula

in which
X has the above-mentioned meaning, preferably chlorine, in the presence, as a catalyst, of a metal, an anhydrous metal halide, a Lewis acid, a nitrogen-alkylated lactam or an N,N-disubstituted carboxylic acid amide or phosphoric acid amide, optionally in combination with elementary sulphur, iodine or an alkali metal iodide, at a temperature of from 0° to 170° C.

Preferably, R denotes alkyl with 1 to 15 carbon atoms; halogenoalkyl (preferably chloroalkyl or bromalkyl) with 1 to 12 carbon atoms; alkylthioalkyl or alkoxyalkyl in each case with 2 to 10 carbon atoms; cycloalkyl with 5 to 7 carbon atoms; naphthyl; benzyl; phenyl, which optionally carries one or more substituents selected from alkoxy with 1 to 4 carbon atoms, alkyl with 1–4 carbon atoms, chlorine, bromine, iodine, fluorine, trifluoromethyl, nitro and methylmercapto; or a pyrimidyl, pyridyl or benzthiazolyl group.

In especially preferred embodments, R represents an alkyl radical with 1 to 6 carbon atoms, in which the hydrogen atoms bonded to the carbon atoms can be entirely or partially replaced by chlorine or bromine, or represents a phenyl radical which optionally carries one or more substituents selected from chlorine, bromine, fluorine, nitro, trifluoromethyl, methyl, methoxy and methylmercapto.

The method according to the invention has a number of advantages over the known methods for the preparation of dithiophosphoric acid ester dihalides. Thus, the present method only requires easily accessible starting materials, which can be reacted in an easily regulated one-pot process, and with high yields, to give the desired products. The dithiophosphoric acid ester halides obtainable in accordance with the process can be isolated from the reaction mixture by simple operations, such as distillation or crystallization. A further feature to be singled out is that the process according to the invention does not pollute the environment. The only by-product formed in the reactions is hydrogen halide, which can be removed easily. The catalysts to be used can be employed repeatedly, so that it is not necessary to discharge them from the process after they have been used once. Furthermore, the process can be used to obtain dithiophosphoric acid ester halides with a great variety of possible substituents; it is not restricted to certain representatives of this category of compounds such as, for example, to the preparation of dithiophosphoric acid alkyl ester dichlorides.

If, for example, n-propylmercaptan and thiophosphoryl chloride are used as starting materials and a catalyst is used, the course of the reaction can be represented by the following equation:

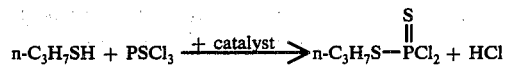

The thiol compounds which according to the invention can be used as starting materials are known and can be prepared, for example, in accordance with the methods described in Houben-Weyl, op. cit., Volume IX, page 3 et seq. Some thiophenols which are difficult to obtain in accordance with the processes specified there can be obtained by the method of Kwart and Newman, J. Org. Chem. 31, 410 [1966], and M. S. Newman et al., ibid. 31, 3 980 [1966].

The use of a solvent or diluent when carrying out the process is not absolutely essential, but halogenated hydrocarbons, such as dichloroethane, monochlorobenzene or dichlorobenzene, can be employed. The reaction according to the invention is carried out — as already mentioned — in the presence of a metal, such as zinc powder, iron powder, copper powder or aluminum powder, or of an anhydrous metal halide, such as iron-(III) chloride, copper(I) chloride, cobalt chloride, zinc chloride or nickel chloride, or of a Lewis acid, such as boron trifluoride, antimony pentachloride, titanium tetrachloride or tin tetrachloride as a catalyst. Furthermore, nitrogen-alkylated lactams and N,N-disubstituted amides of carboxylic acids and phosphoric acids, such as 1-methyl-pyrrolidone, N,N-dimethylformamide, N,N-dimethylacetamide, N-methylacetanilide, N-methylformanilide, hexamethylphosphoric acid triamide or hexamethylthiophosphoric acid triamide, N,N-dimethylamidophosphoric acid dichloride or N,N-dimethylamidothiophosphoric acid dichloride and N,N-dimethyldiamidophosphoric acid chloride, if appropriate in combination with elementary sulphur, elementary iodine, potassium iodide or the metal halides described above, can be employed as catalysts.

Preferably, anhydrous zinc chloride or N,N-dimethylformamide, by themselves or in combination with elementary sulphur or elementary iodine, are used for the reaction.

The reaction according to the invention is carried out at temperatures between about 0° and +170° C, preferably between about 10° and 150° C, and in general under normal pressure. However, it can also be carried out under slight to moderate excess pressure. In general, the reaction is allowed to take place at pressures of between 0.5 and 5 atmospheres.

In carrying out the process according to the invention, about 1.1 to 2, preferably about 1.4 to 1.9, moles of thiophosphoryl halide (III) and about 0.001 to 0.1, preferably about 0.005 to 0.1, mole of catalyst are employed per mole of the thiol compound (II).

According to a particular embodiment, the process for the preparation of the dithiophosphoric acid ester dihalides which are to be purified by distillation can also be carried out continuously. In this process, after completion of the reaction and after distilling off the excess thiophosphoryl halide and the dithiophosphoric acid ester dihalide formed, the distillation residue, which contains the catalyst, is again reacted, without changing the reaction vessel, with thiophosphoryl halide and the thiol compound.

The method of working up of the reaction mixture depends on the physical properties of the dithiophosphoric acid ester dihalide prepared. The dithiophosphoric acid alkyl ester dichlorides are in general liquid and can be separated off by distillation under reduced pressure. Some dithiophosphoric acid aryl ester dichlorides and the compounds containing a heterocyclic radical are obtained in the form of solids and can be purified, after distilling off the excess thiophosphoryl chloride, by recrystallization from hydrocarbons, such as toluene or ligroin.

The dithiophosphoric acid ester dihalides which can be prepared by the process according to the invention may be used as intermediates for the synthesis of insecticidal thiophosphoric acid esters.

The process according to the invention is illustrated in the preparative Examples which follow:

EXAMPLE 1

31 g (0.5 mole) of ethylmercaptan were added dropwise to a mixture of 119 g (0.7 mole) of thiophosphoryl chloride, 0.9 g (0.012 mole) of dry N,N-dimethylformamide and 0.5 g (0.016 mole) of sulphur at 30° to 35° C. The temperature of the mixture was slowly raised to 130° – 135° C over the course of 1 to 2 hours, the batch was stirred for a further 6 hours at 135° – 145° C and the excess thiophosphoryl chloride was distilled off under reduced pressure at 30° to 40° C. 80 g (82% of theory) of dithiophosphoric acid ester dichloride of boiling point 75° to 76° C/4 to 5 mm Hg were obtained by distillation from the liquid residue.

EXAMPLE 2

76 g (1 mole) of n-propylmercaptan were added dropwise to a mixture of 288 g (1.7 moles) of thiophosphoryl chloride, 0.9 g (0.012 mole) of dry N,N-dimethylformamide and 0.5 g (0.002 mole) of iodine at 30° to 35° C. The temperature of the reaction mixture was slowly raised to 130° – 135° C over the course of 1 to 2 hours, the batch was then stirred for 9 hours at 135° to 145° C, and after distilling off the excess thiophosphoryl chloride the liquid residue was distilled under reduced pressure. 175 g (84% of theory) of dithiophosphoric acid n-propyl ester dichloride of boiling point 105° to 106° C/10 mm Hg were obtained.

EXAMPLE 3

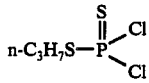 (2)

76 g (1 mole) of n-propylmercaptan were added dropwise to a mixture of 237 g (1.4 moles) of thiophosphoryl chloride and 1 g (0.0073 mole) of anhydrous zinc chloride at 50° to 60° C. The temperature of the mixture was raised slowly to 130°–135° C over the course of 1 to 2 hours, the batch was then stirred for a further 6 hours at 135° to 145° C, the excess thiophosphoryl chloride was removed under reduced pressure at 30° to 40° C and the residue was distilled. 115 g (ca. 55% of theory) of dithiophosphoric acid n-propyl ester dichloride of boiling point 104° to 106° C/10 mm Hg were obtained.

EXAMPLE 4

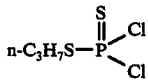 (2)

A mixture of 119 g (0.7 mole) of thiophosphoryl chloride, 1 g (0.0056 mole) of hexamethylphosphoric acid triamide and 38 g (0.5 mole) of n-propylmercaptan was slowly heated to 130° C over the course of about 2 hours. The batch was then stirred for 6 hours at 135° to 140° C and after distilling off the excess thiophosphoryl chloride the liquid residue was distilled under reduced pressure. 73 g (ca. 70% of theory) of dithiophosphoric acid n-propyl ester dichloride of boiling point 104° to 106° C/10 mm Hg were obtained.

EXAMPLE 5

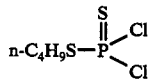 (3)

90 g (1 mole) of n-butyl mercaptan were added dropwise to a mixture of 237 g (1.4 moles) of thiophosphoryl chloride, 0.9 g (0.012 mole) of dry N,N-dimethylformamide and 0.5 g (0.002 mole) of iodine at 50° to 60° C. The temperature of the mixture was then slowly raised to 125° – 135° C over the course of 1 to 2 hours, the batch was stirred for 6 hours at 135° to 140° C and after distilling off the excess thiophosphoryl chloride in vacuo the residue was distilled under a pressure of 5 mm Hg. The fraction of boiling range 88° to 92° C (176 g; ca. 79% of theory) was collected; on the basis of the boiling point, it was identical to authentic dithiophosphoric acid n-butyl ester.

EXAMPLE 6

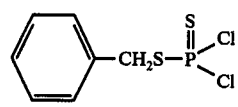 (4)

Analogously to the method described in Example 5, 119 g (0.7 mole) of thiophosphoryl chloride, 0.9 g (0.012 mole) of dry N,N-dimethylformamide, 0.5 g (0.002 mole) of iodine and 66 g of a 94% strength benzyl mercaptan (0.5 mole) gave 95 g (ca. 74% of theory) of dithiophosphoric acid benzyl ester dichloride of boiling point 158° to 160° C/4 mm Hg.

EXAMPLE 7

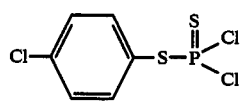 (5)

A mixture of 119 g (0.7 mole) of thiophosphoryl chloride, 72.3 g (0.5 mole) of 4-chlorothiophenol, 0.9 g (0.012 mole) of dry N,N-dimethylformamide and 0.5 g (0.0016 mole) of sulphur was heated for 3 hours to 135°–145° C and after distilling off the thiophosphoryl chloride under reduced pressure the solid residue was recrystallized from ligroin (boiling point 40° to 80° C). 105 g (ca. 76% of theory) of dithiophosphoric acid 4-chlorophenyl ester dichloride were obtained in the form of a colorless, crystalline substance of melting point 64° C.

| Analysis: | Cl | S |
| --- | --- | --- |
| calculated: | 38.3% | 23.1% |
| found: | 38.6% | 23.6% |

The following compounds could also be prepared by methods analogous to those described in the preceding Examples:

| Formula | Yield (% of theory) | B.pt ° C/ mm Hg |
| --- | --- | --- |
| CH₃—S—P(=S)(Cl)Cl  (6) | 71 | 59–62/4 |
| i-C₃H₇S—P(=S)(Cl)Cl  (7) | 56 | 69–71/4 |
| i-C₄H₉S—P(=S)(Cl)Cl  (8) | 66 | 84/4 |
| n-C₈H₁₇—S—P(=S)(Cl)Cl  (9) | 70 | 152–154/4–5 |
| C₂H₅O—CH₂—CH₂—S—P(=S)(Cl)Cl  (10) | 61 | 101–103/4 |

-continued

| Formula | Yield (% of theory) | B.pt ° C/ mm Hg |
|---|---|---|
| 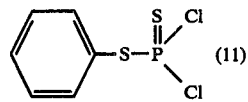 (11) | 67 | 120–124/4 |

It will be appreciated that the instant specification and examples are set forth by way of illustration and not limitation, and that various modifications and changes may be made without departing from the spirit and scope of the present invention.

What we claim is:

1. A process for the preparation of a dithiophosphoric acid ester dihalide of the formula

in which
X is chlorine, bromine, fluorine or iodine, and
R is an alkyl radical with up to 15 carbon atoms optionally substituted by halogen, by alkoxy or by alkylthio, a cycloaliphatic radical with 5 or 6 ring members, an aralkyl radical with 7 to 15 carbon atoms or an aryl or heterocyclic radical, comprising reacting a thiol compound of the formula

with a thiophosphoryl halide of the formula

in the presence of a catalyst selected from the group consisting of a metal, an anhydrous metal halide, a Lewis acid, a nitrogen-alkylated lactam or an N,N-disubstituted carboxylic acid amide or phosphoric acid amide at a temperature of about 0° to 170° C.

2. A process according to claim 1 in which R is alkyl with 1 to 15 carbon atoms; halogenoalkyl with 1 to 12 carbon atoms; alkylthioalkyl or alkoxyalkyl in each case with 2 to 10 carbon atoms; cycloalkyl with 5 to 7 carbon atoms; naphthyl; benzyl; phenyl; phenyl substituted by at least one of alkoxy with 1 to 4 carbon atoms, alkyl with 1-4 carbon atoms, chlorine, bromine, iodine, fluorine, trifluoromethyl, nitro, and methylmercapto; or a pyrimidyl, pyridyl or benzthiazolyl group.

3. A process according to claim 2, in which R is an alkyl radical with 1 to 6 carbon atoms, an alkyl radical with 1 to 6 carbon atoms substituted by at least one of chlorine and bromine, phenyl, or phenyl substituted by at least one of chlorine, bromine, fluorine, nitro, trifluoromethyl, methyl, methoxy and methylmercapto.

4. A process according to claim 1, in which X is chlorine.

5. A process according to claim 1, in which the catalyst is at least one member selected from the group of zinc powder, iron powder, copper powder, aluminum powder, iron(III) chloride, copper(I) chloride, cobalt chloride, zinc chloride, nickel chloride, boron trifluoride, antimony pentachloride, titanium tetrachloride, tin tetrachloride, 1-methyl-pyrrolidone, N,N-dimethylformamide, N,N-dimethylacetamide, N-methylacetanilide, N-methylformanilide, hexamethylphosphoric acid triamide, hexamethylthiophosphoric acid triamide, N,N-dimethylamidophosphoric acid dichloride, N,N-dimethylamidothiophosphoric acid dichloride and N,N-dimethyldiamidophosphoric acid chloride, alone or in combination with at least one member selected from the group consisting of elementary sulfur, elementary iodine and an alkali metal iodide.

6. A process according to claim 1, in which the catalyst comprises at least one of anhydrous zinc chloride and N,N-dimethylformamide, alone or in combination with at least one of elementary sulfur and elementary iodine.

7. A process according to claim 1, in which about 1.1 to 2 moles of thiophosphoryl halide and about 0.001 to 0.1 mole of catalyst are employed per mole of thiol compound, and the reaction is carried out at about 10° to 150° C and at a pressure of between about 0.5 and 5 atmospheres.

8. A process according to claim 7, in which about 1.4 to 1.9 moles of thiophosphoryl halide and about 0.005 to 0.1 mole of catalyst are employed per mole of thiol compound.

9. A process according to claim 1, including the further steps of continuously distilling off the dithiophosphoric acid ester halide formed and the excess thiophosphoryl halide after completion of the reaction, and reacting the distillation residue containing the catalyst with further quantities of thiophosphoryl halide and thiol compound.

10. A process according to claim 9, in which R is an alkyl radical with 1 to 6 carbon atoms, an alkyl radical with 1 to 6 carbon atoms substituted by at least one of chlorine and bromine, phenyl, or phenyl substituted by at least one of chlorine, bromine, fluorine, nitro, trifluoromethyl, methyl, methoxy and methylmercapto, X is chlorine, about 1.4 to 1.9 moles of thiophosphoryl halide and about 0.005 to 0.1 mole of catalyst are employed per mole of thiol compound, the reaction is carried out at about 10° to 150° C and at a pressure of between about 0.5 and 5 atmospheres, and the catalyst comprises at least one of anhydrous zinc chloride and N,N-dimethylformamide, alone or in combination with at least one of elementary sulphur and elementary iodine.

* * * * *